(12) United States Patent
Blythe et al.

(10) Patent No.: US 7,605,270 B2
(45) Date of Patent: Oct. 20, 2009

(54) POLYMORPHIC FORMS OF (S).-TETRAHYDROFURAN-3-YL-3-(3-(3-METHOXY-4-(OXAZOL-5-YL) PHENYL) UREIDO) BENZYLCARBAMATE

(75) Inventors: Todd Blythe, Georgetown, MA (US); Alex Eberlin, Cambridge (GB); Michael Hurrey, Maynard, MA (US); David Jonaitis, Lafayette, IN (US); Philip Nyce, Millbury, MA (US); Stephan Parent, West Lafayette, IN (US); John Snoonian, Bolton, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 74 days.

(21) Appl. No.: 11/429,811

(22) Filed: May 8, 2006

(65) Prior Publication Data

US 2007/0281980 A1    Dec. 6, 2007

Related U.S. Application Data

(60) Provisional application No. 60/679,021, filed on May 9, 2005.

(51) Int. Cl.
*C07D 263/32*    (2006.01)
(52) U.S. Cl. ..................................... 548/236
(58) Field of Classification Search .................. 548/236
See application file for complete search history.

(56) References Cited

U.S. PATENT DOCUMENTS 6,541,496 B1 * 4/2003 Armistead et al. .......... 514/374

OTHER PUBLICATIONS

Byrn, et al. ed. "Comparing X-ray Powder Data". Solid State Chemistry of Drugs, 2nd edition, p. 63.*
A. Maureen Rouhi, Chemical & Engineering News, Feb. 24, 2003, pp. 32-35.*
Haleblian et al. Journal of Pharmaceutical Sciences, Aug. 1969, vol. 58, No. 8, pp. 911-929.*

* cited by examiner

*Primary Examiner*—Rebecca L Anderson
*Assistant Examiner*—Shawquia Young
(74) *Attorney, Agent, or Firm*—Michael C. Badia

(57) ABSTRACT

The present invention relates to polymorphic forms of (S)-tetrahydrofuran-3-yl 3-(3-(3-methoxy-4-(oxazol-5-yl)phenyl)ureido)benzylcarbamate (Compound 1):

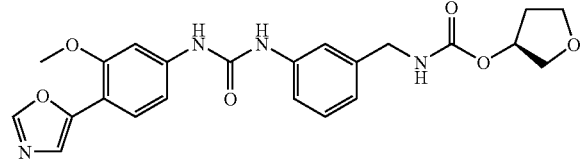

and pharmaceutical compositions thereof. The present invention also relates to processes to prepare compound 1 and pharmaceutical compositions thereof. Compound 1 is an IMPDH inhibitor useful in treating IMPDH-mediated diseases such as immune system related diseases, viral diseases, and cancers.

10 Claims, 12 Drawing Sheets

DSC

DSC

POLYMORPHIC FORMS OF (S).-TETRAHYDROFURAN-3-YL-3-(3-(3-METHOXY-4-(OXAZOL-5-YL) PHENYL) UREIDO) BENZYLCARBAMATE

CROSS REFERENCE TO RELATED APPLICATIONS

This application claims the benefit under 35 U.S.C. § 119 of U.S Provisional application Ser. No. 60/679,021 filed May 9, 2005, the entire contents of which is incorporated herein by reference.

TECHNICAL FIELD OF THE INVENTION

The present invention relates to polymorphic forms of (S)-tetrahydrofuran-3-yl 3-(3-(3-methoxy-4-(oxazol-5-yl)phenyl)ureido)benzylcarbamate, processes therein, pharmaceutical compositions thereof, and methods therewith.

BACKGROUND OF THE INVENTION

The present invention relates to polymorphic forms of (S)-tetrahydrofuran-3-yl 3-(3-(3-methoxy-4-(oxazol-5-yl)phenyl)ureido)benzylcarbamate having the structure below (hereinafter "Compound 1"):

The present invention also relates to processes to prepare polymorphic forms of Compound 1.

Compound 1 is a potent IMPDH inhibitor useful in treating IMPDH-mediated diseases. Compound 1, compositions thereof, and methods therewith are disclosed in U.S. Pat. Nos. 5,807,876; 6,054,472; 6,344,465; and 6,541,496 (hereinafter "the Compound 1 patents"), the entire disclosures of which are incorporated herein by reference.

SUMMARY OF THE INVENTION

The present invention provides five polymorphic forms of Compound 1, namely, Form A1, Form B2, Form C3, Form D4, and Form E5. The present invention also relates to processes for making these polymorphic forms. The invention also relates to the use of these polymorphic forms in therapeutic methods and in the preparation of pharmaceutical compositions comprising such polymorphic forms. The present invention also relates to an amorphous form of Compound 1, and processes for producing such an amorphous form.

Figure 1:
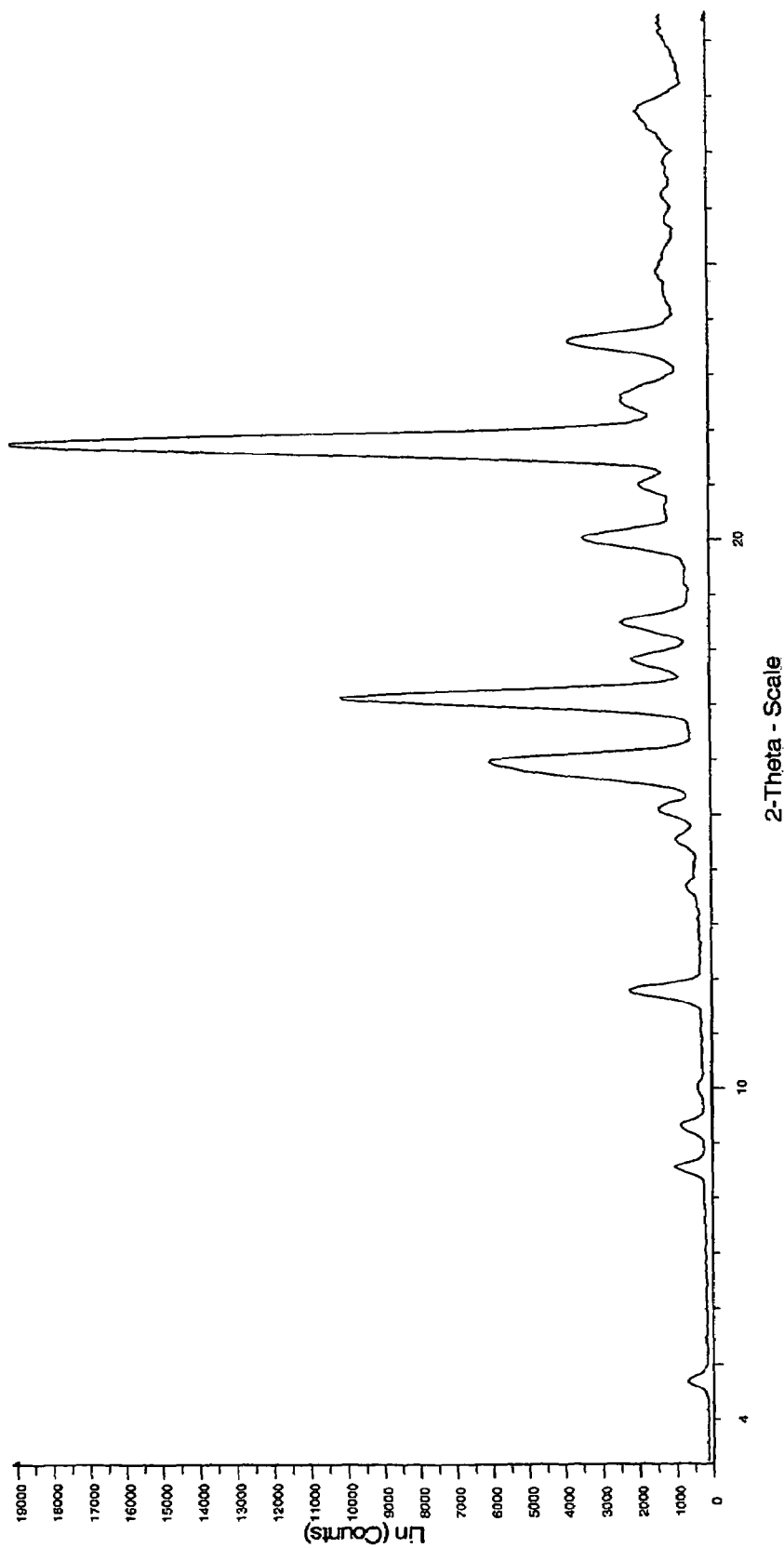
FIG. 1 is an x-ray powder diffraction pattern (XRPD) of Form A1 of (S)-tetrahydrofuran-3-yl 3-(3-(3-methoxy-4-(oxazol-5-yl)phenyl)ureido)benzylcarbamate.
Figure 2:
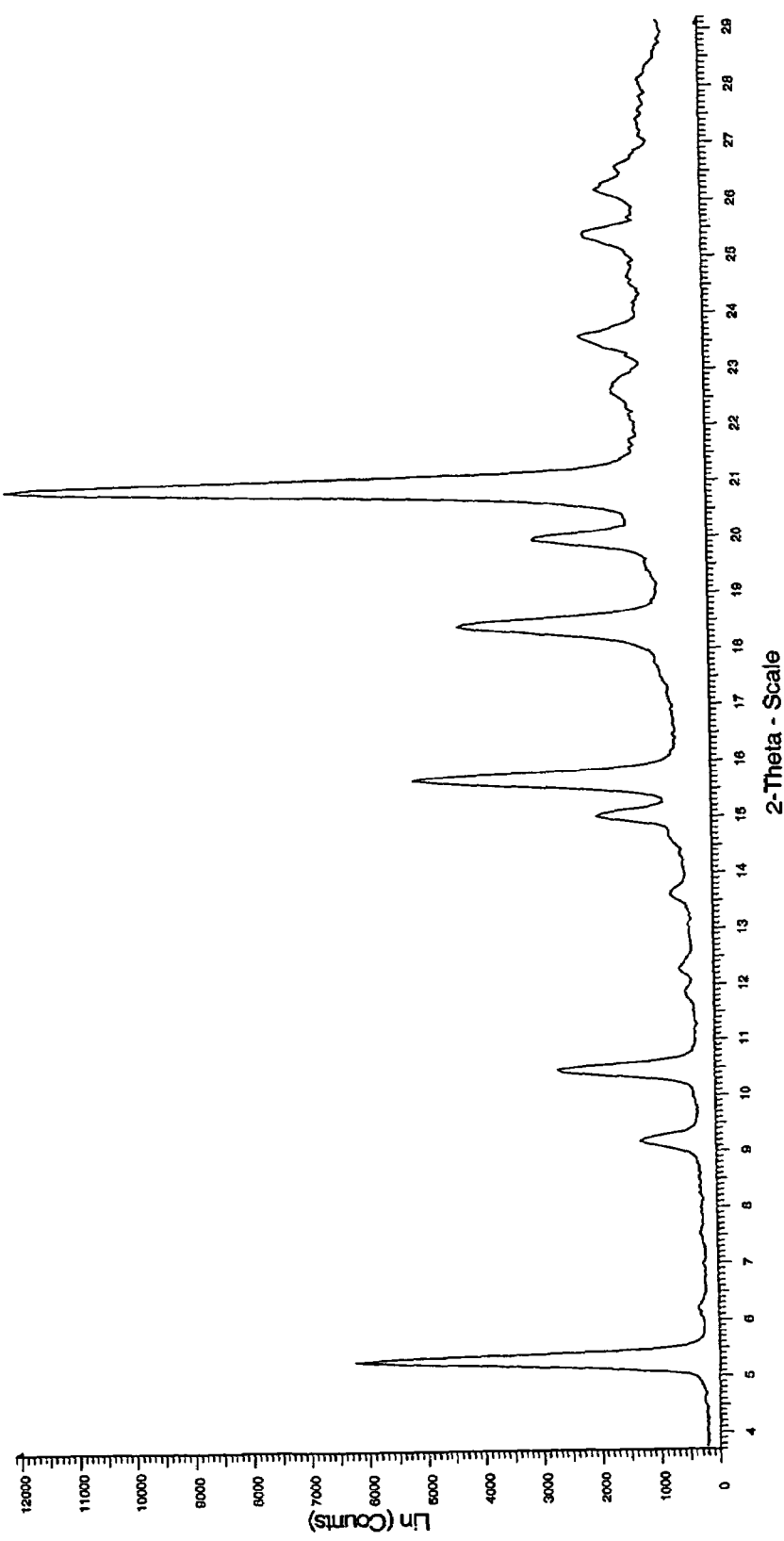
FIG. 2 is an XRPD of Form B2 of (S)-tetrahydrofuran-3-yl 3-(3-(3-methoxy-4-(oxazol-5-yl)phenyl)ureido)benzylcarbamate.
Figure 3:
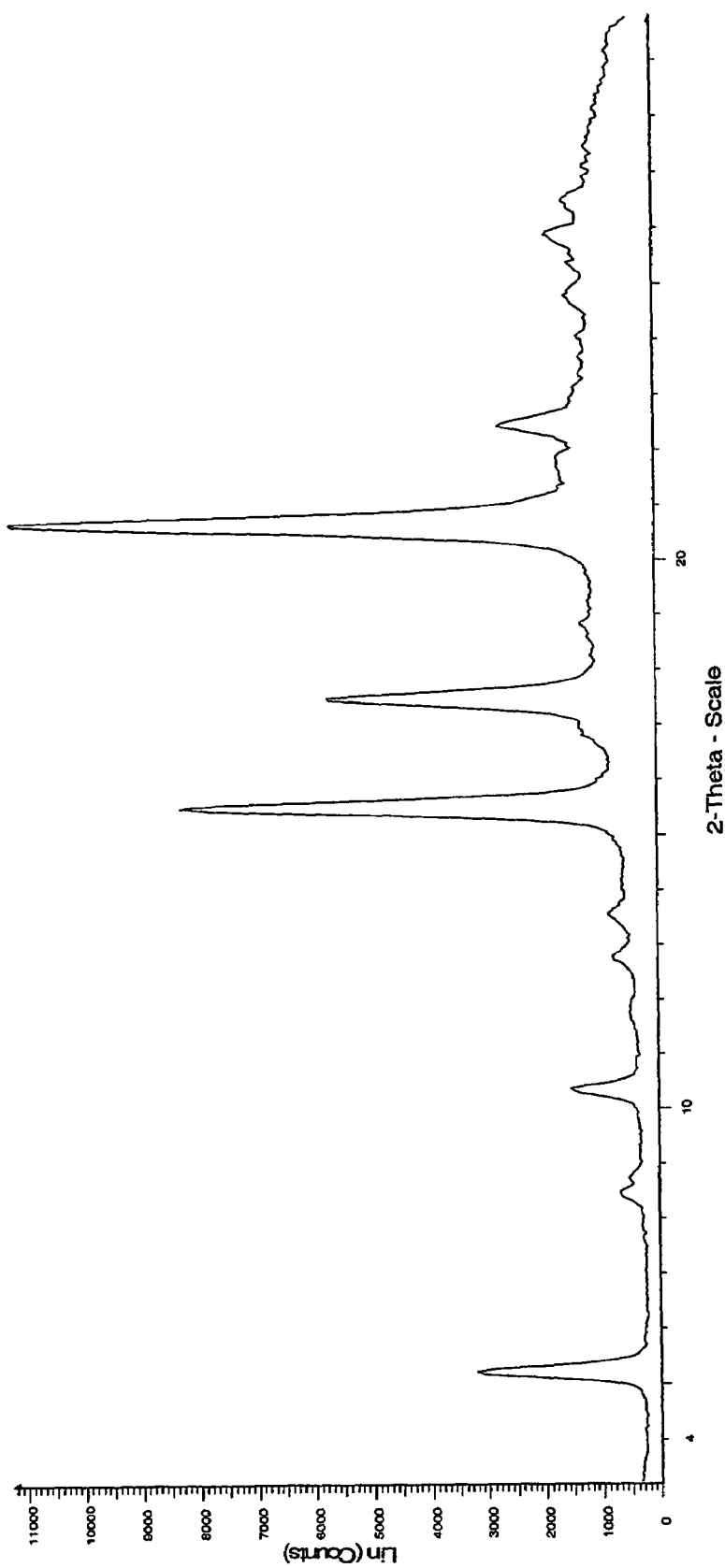
FIG. 3 is an XRPD of Form C3 of (S)-tetrahydrofuran-3-yl 3-(3-(3-methoxy-4-(oxazol-5-yl)phenyl)ureido)benzylcarbamate.
Figure 4:
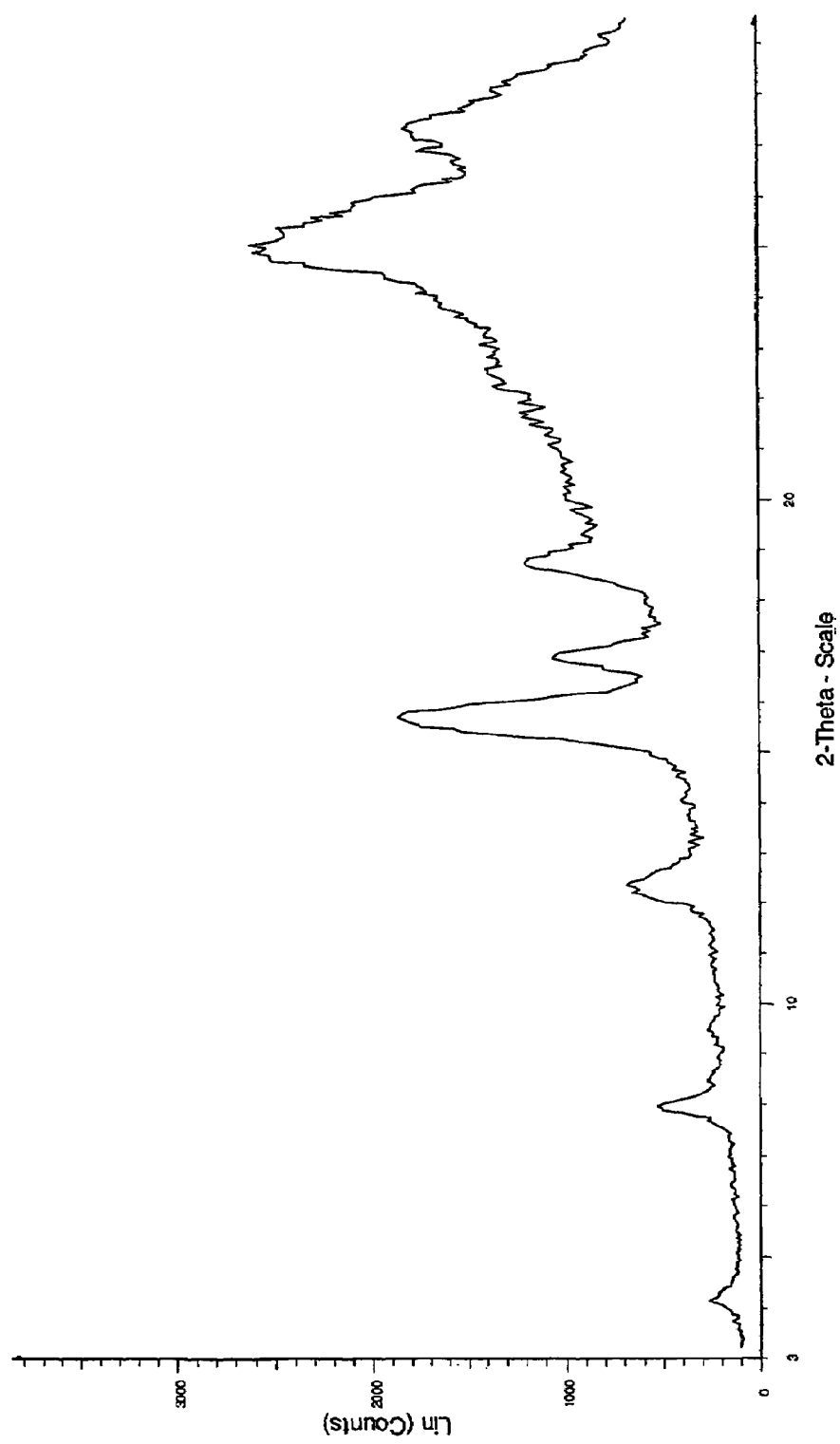
FIG. 4 is an XRPD of Form D4 of (S)-tetrahydrofuran-3-yl 3-(3-(3-methoxy-4-(oxazol-5-yl)phenyl)ureido)benzylcarbamate, HCl salt.
Figure 5:
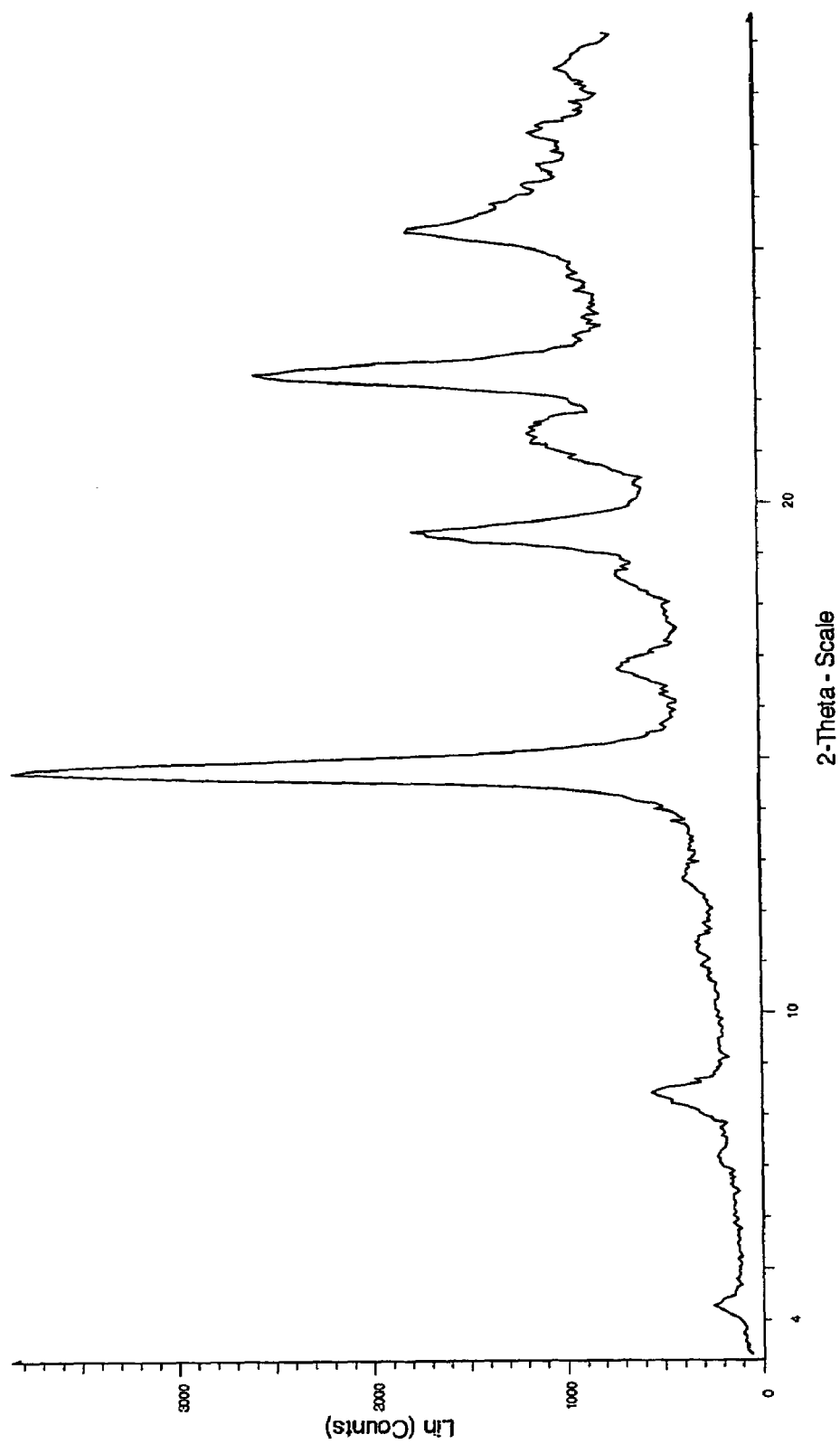
FIG. 5 is an XRPD of Form E5 of (S)-tetrahydrofuran-3-yl 3-(3-(3-methoxy-4-(oxazol-5-yl)phenyl)ureido)benzylcarbamate, HCl salt.
Figure 6:
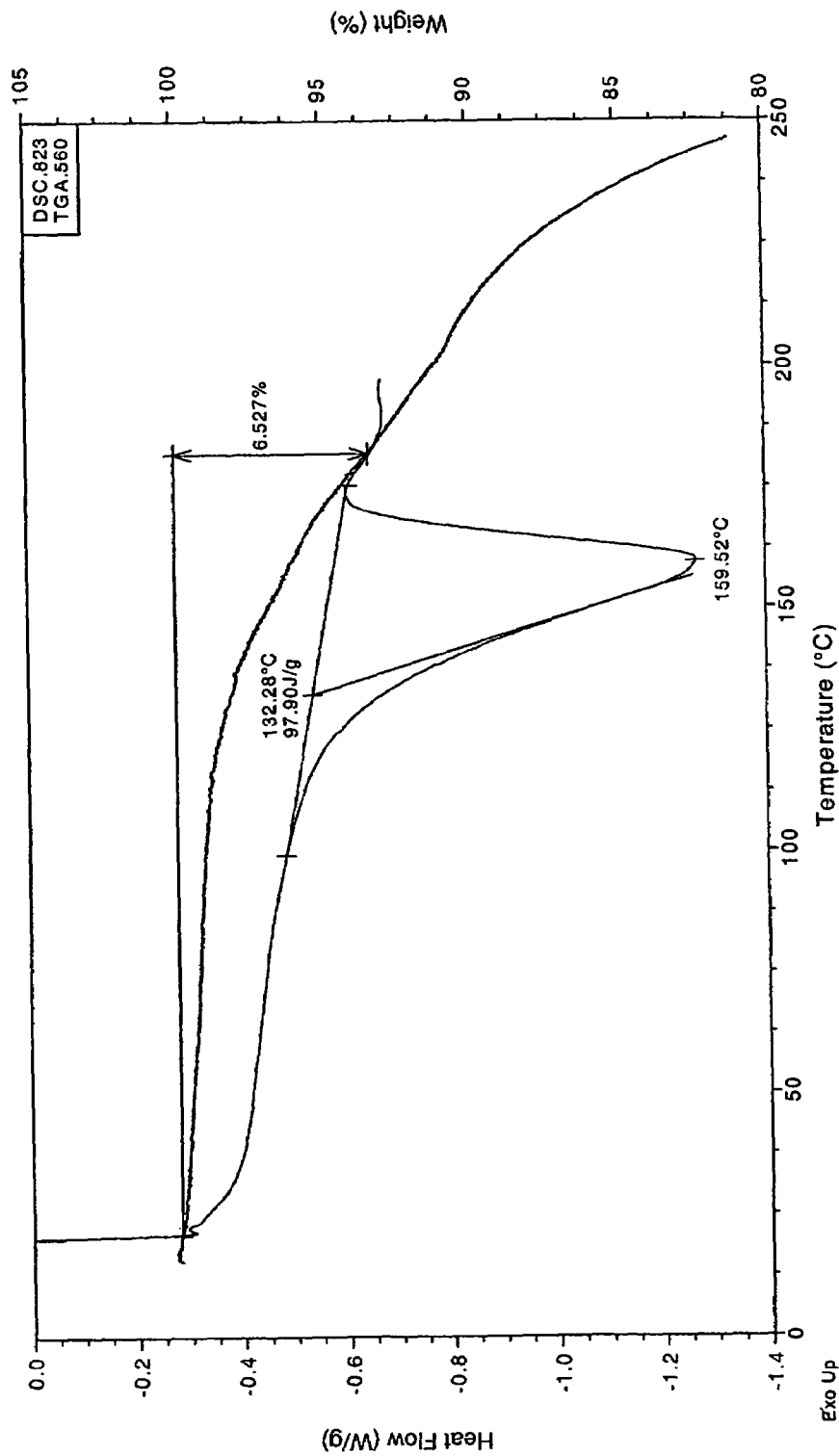
FIG. 6 is a combination Differential Scanning Calorimetry (DSC) thermogram and thermogravimetric analysis (TGA) of Form D4 of (S)-tetrahydrofuran-3-yl 3-(3-(3-methoxy-4-(oxazol-5-yl)phenyl)ureido)benzylcarbamate, HCl salt.
Figure 7:
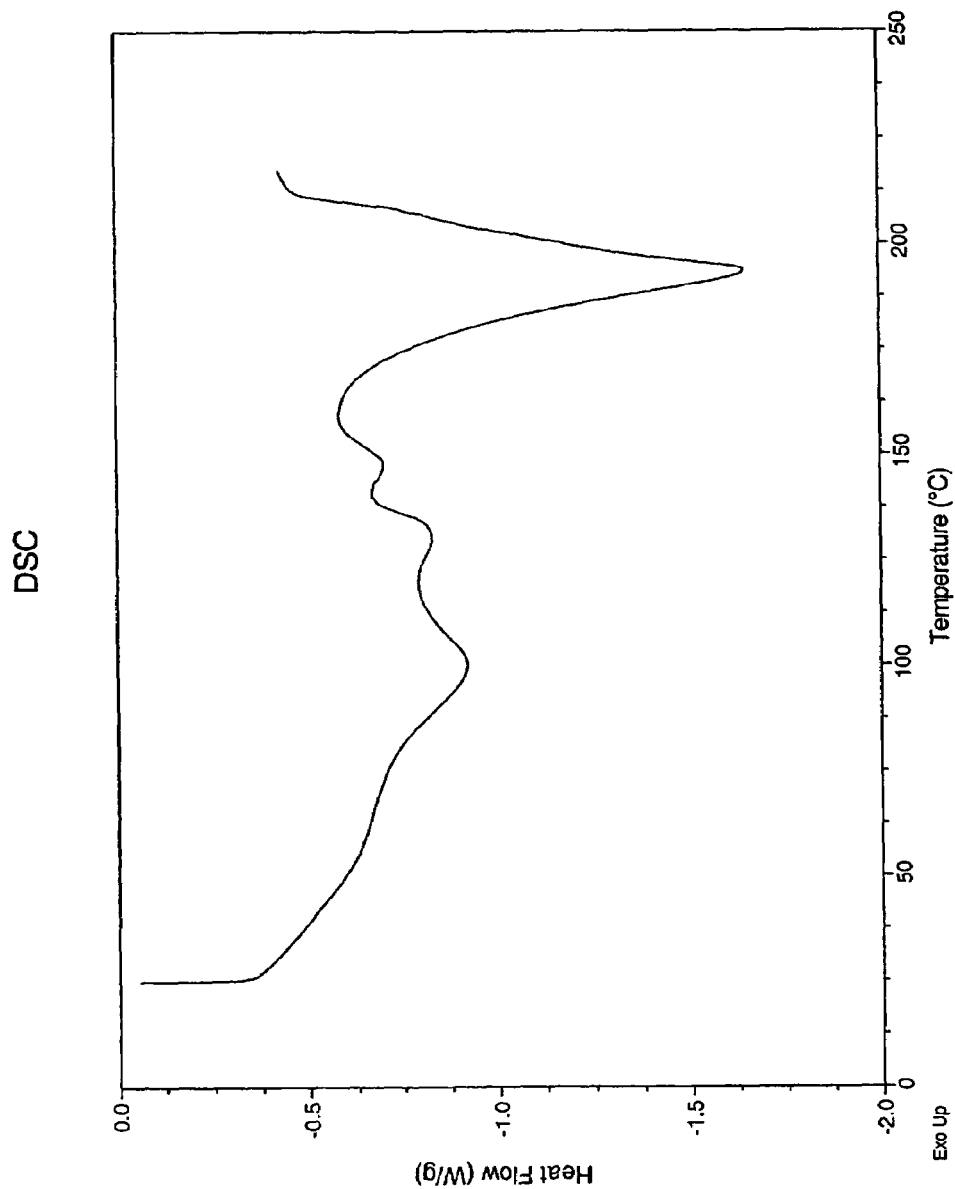
FIG. 7 is a DSC thermogram of Form E5 of (S)-tetrahydrofuran-3-yl 3-(3-(3-methoxy-4-(oxazol-5-yl)phenyl)ureido)benzylcarbamate, HCl salt.
Figure 8:
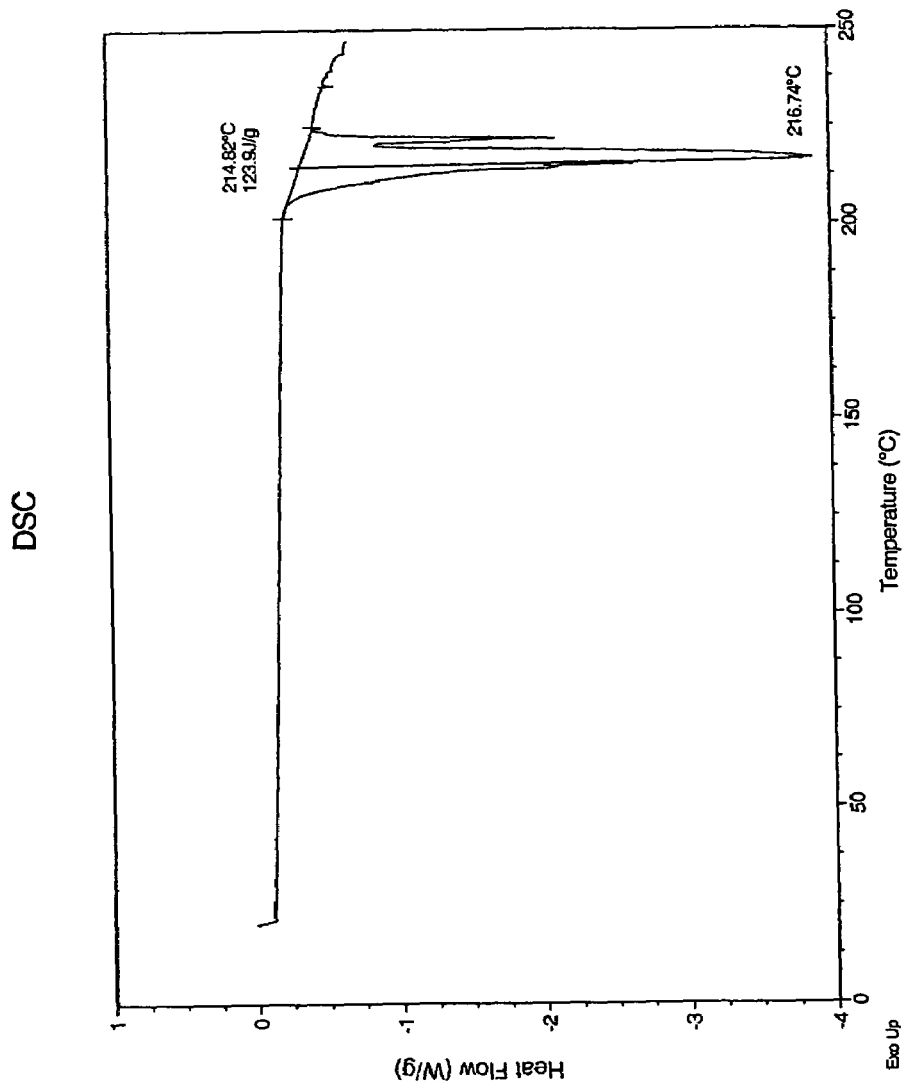
FIG. 8 is a DSC thermogram of Form A1 of (S)-tetrahydrofuran-3-yl 3-(3-(3-methoxy-4-(oxazol-5-yl)phenyl)ureido)benzylcarbamate.
Figure 9:
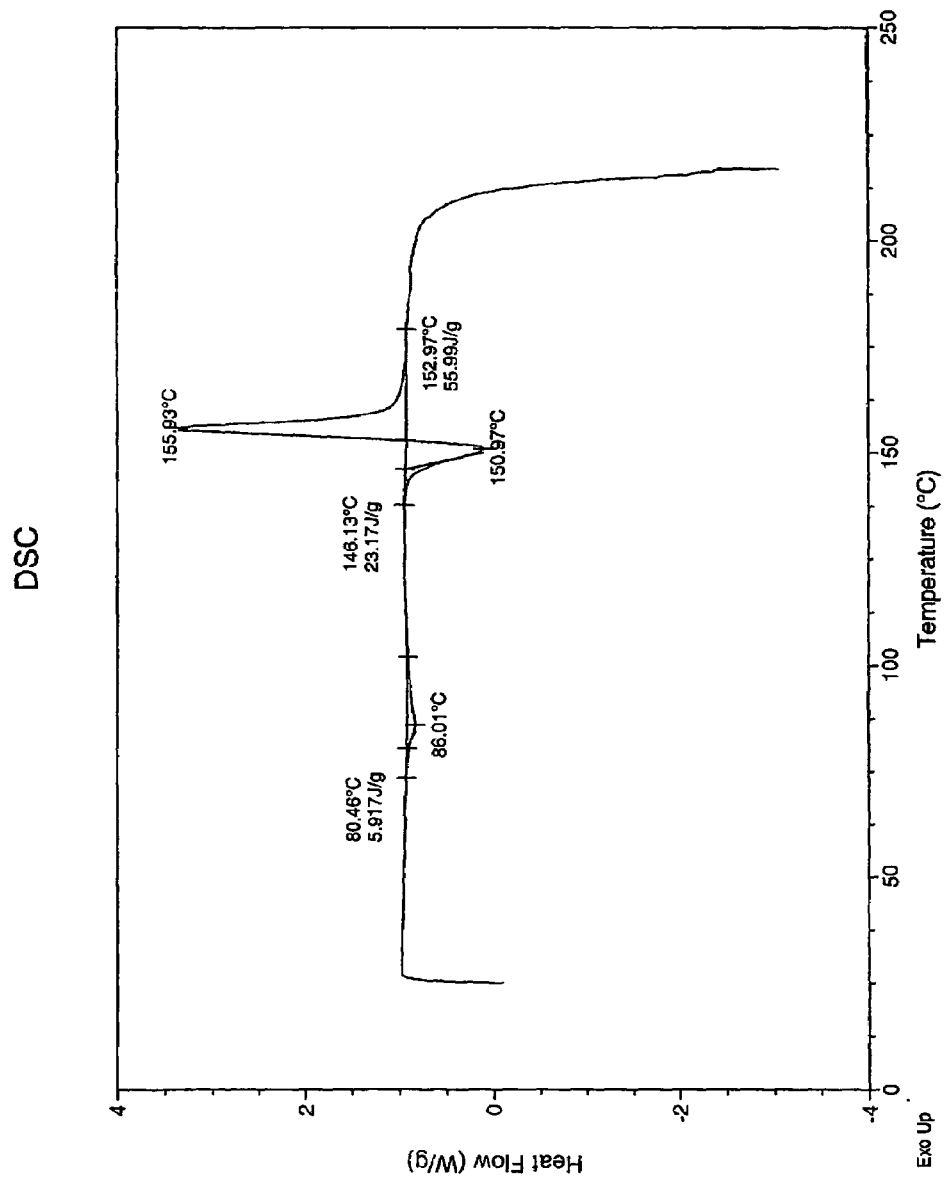
FIG. 9 is a DSC thermogram of Form B2 of (S)-tetrahydrofuran-3-yl 3-(3-(3-methoxy-4-(oxazol-5-yl)phenyl)ureido)benzylcarbamate.
Figure 10:
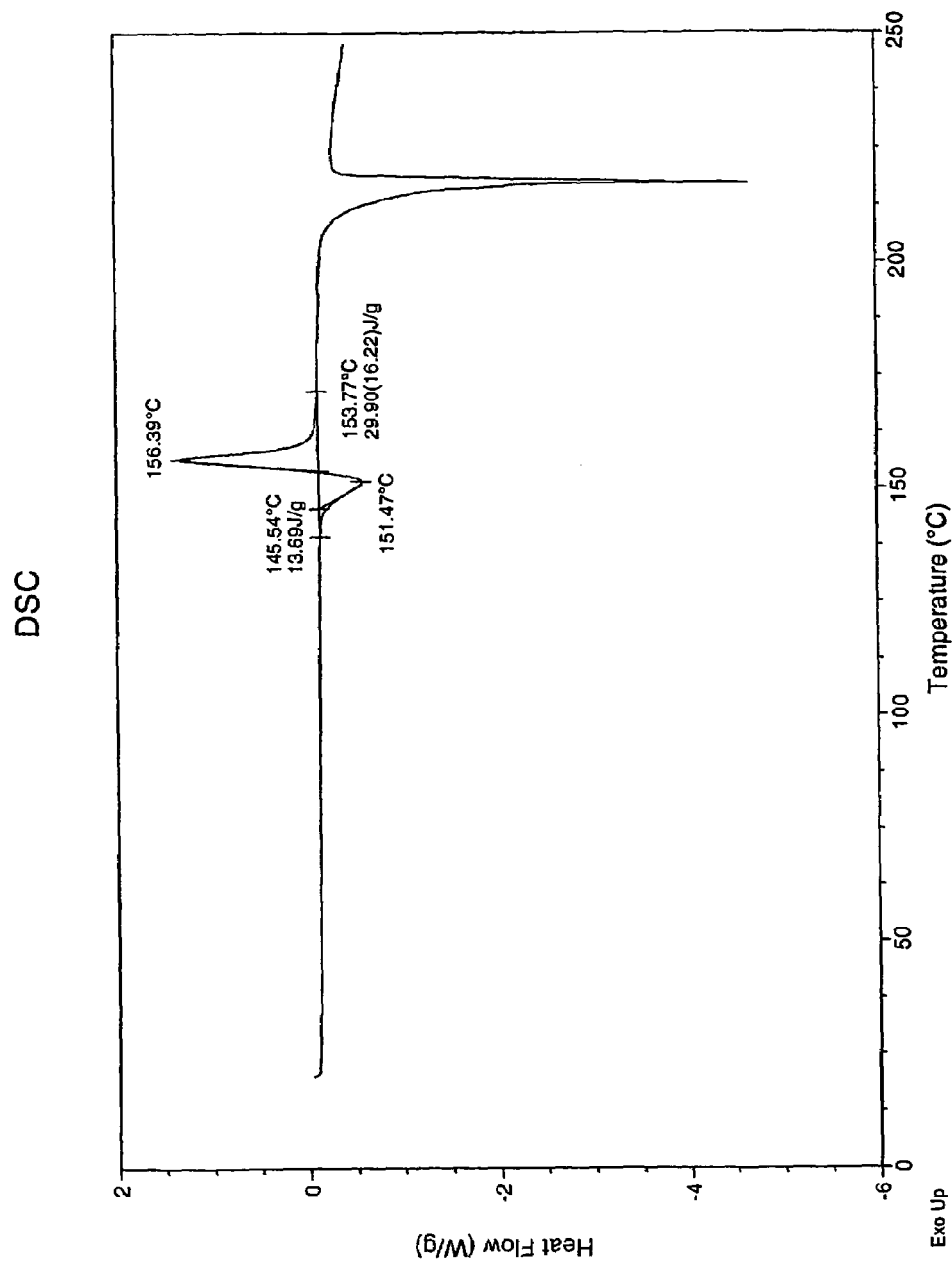
FIG. 10 is a DSC thermogram of Form C3 of (S)-tetrahydrofuran-3-yl 3-(3-(3-methoxy-4-(oxazol-5-yl)phenyl)ureido)benzylcarbamate.
Figure 11:
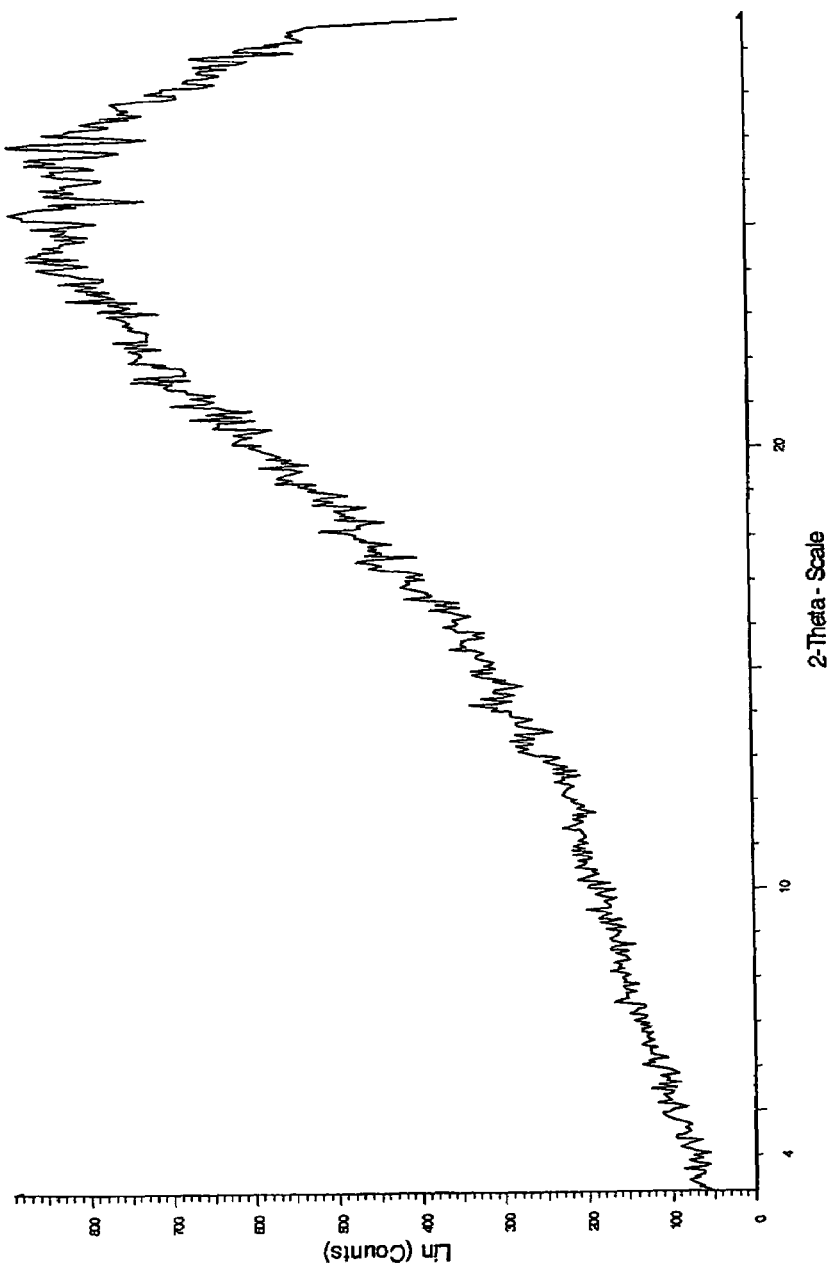
FIG. 11 is an XRPD of amorphous (S)-tetrahydrofuran-3-yl 3-(3-(3-methoxy-4-(oxazol-5-yl)phenyl)ureido)benzylcarbamate.
Figure 12:
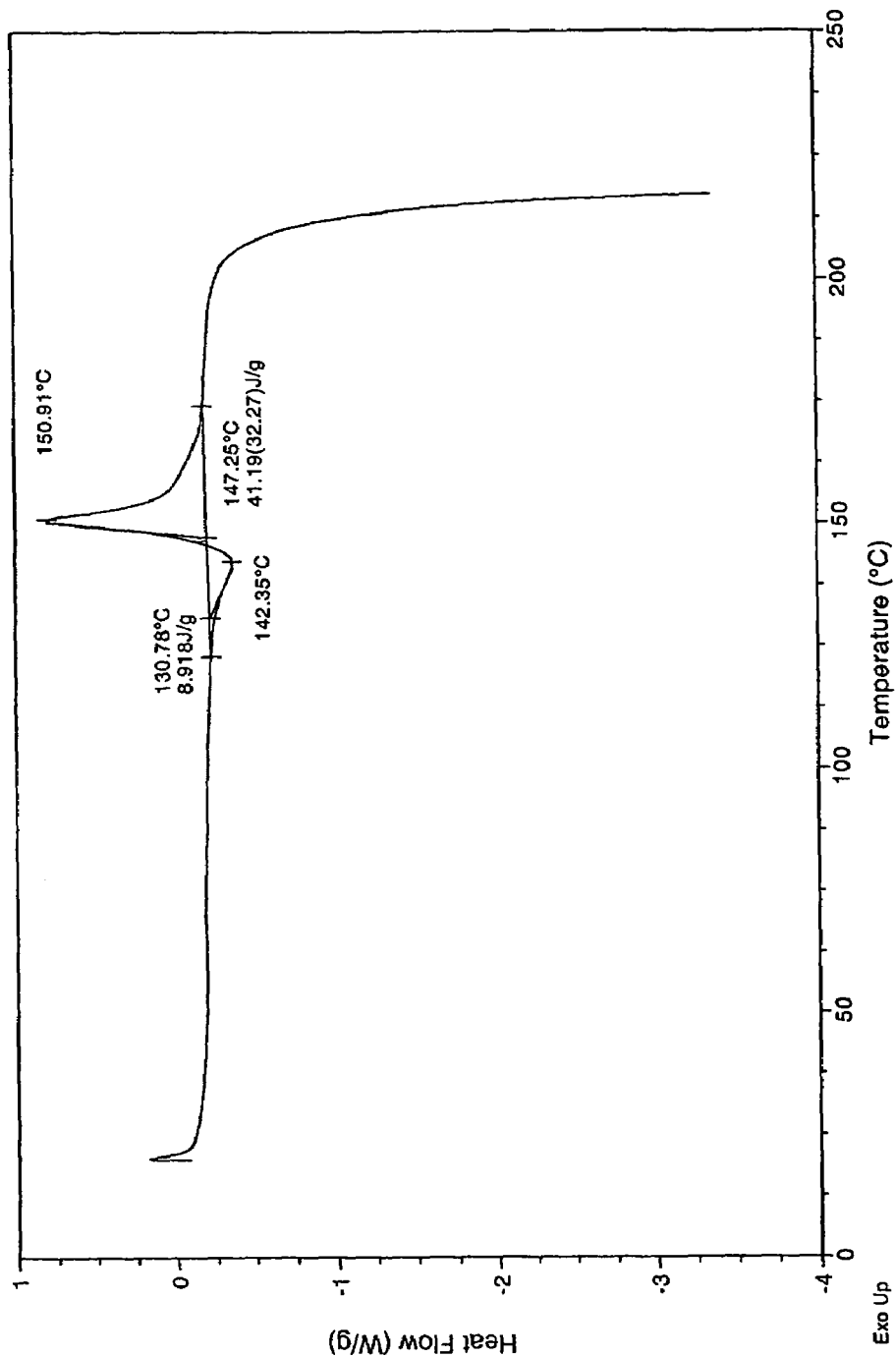
FIG. 12 is a DSC thermogram of amorphous (S)-tetrahydrofuran-3-yl 3-(3-(3-methoxy-4-(oxazol-5-yl)phenyl)ureido)benzylcarbamate.

DETAILED DESCRIPTION OF THE INVENTION (S)-tetrahydrofuran-3-yl 3-(3-(3-methoxy-4-(oxazol-5-yl)phenyl)ureido)benzylcarbamate (Compound 1) is a potent IMPDH inhibitor useful in treating IMPDH-mediated diseases. Three polymorphic forms of the free base of Compound 1 (Form A1, Form B2, and Form C3) have been identified. Two polymorphic forms of an HCl salt of Compound 1 (Form D4 and Form E5) have also been identified.

The polymorphs of the present invention may occur as racemates, racemic mixtures, and diastereomeric mixtures with all possible isomers and mixtures thereof being included in the present invention.

According to one embodiment, the present invention provides polymorphic Form A1, Form B2, Form C3, Form D4, and Form E5 of Compound 1 with the (S) stereochemistry as indicated in the structure of Compound 1 herein.

According to one embodiment, the present invention provides a polymorphic Form A1 of (S)-tetrahydrofuran-3-yl 3-(3-(3-methoxy-4-(oxazol-5-yl)phenyl)ureido)benzylcarbamate.

According to another embodiment, the present invention provides a substantially pure polymorphic Form A1 of (S)-tetrahydrofuran-3-yl 3-(3-(3-methoxy-4-(oxazol-5-yl)phenyl)ureido)benzylcarbamate, wherein said polymorph comprises less than about 5% by weight of amorphous form.

According to another embodiment, the present invention provides a polymorphic Form A1 of Compound 1 wherein the polymorph has a peak position at about 21.8 degrees 2-theta in an x-ray powder diffraction pattern obtained using Cu K alpha radiation.

According to another embodiment, the present invention provides a polymorphic Form A1 of Compound 1 wherein the polymorph has at least one additional peak position at about 11.8, 16.0, 18.5, 20.1, or 23.6 degrees 2-theta in an x-ray powder diffraction pattern obtained using Cu K alpha radiation.

According to another embodiment, the present invention provides a polymorphic Form A1 of Compound 1 wherein the polymorph exhibits a melting/decomposition endothermic event at about 215° C. as measured by a Differential Scanning Calorimeter (DSC). Depending on the rate of heating or the scan rate at which the DSC analysis is conducted, the calibration standard used, the relative humidity and upon the chemical purity, the endotherms of the respective Forms A1, B2, C3, D4, E5, and amorphous form may vary by about 0.01 to 100° C. above or below the endotherms depicted in the Figures. For any given sample, the observed endotherm may also differ from instrument to instrument; however, it will generally be within the ranges defined herein provided the instruments are calibrated similarly.

According to another embodiment, Form A1 is an anhydrous crystalline form with a melting/decomposition temperature of about 215° C. The DSC shows a single endotherm at about 215° C. which corresponds to the on-set of significant weight loss in the thermogravimetric analysis (TGA). Up to this temperature about a 0.4% weight loss was observed. Form A1 is non-hygroscopic with a water uptake of less than 0.5% at 90% relative humidity (RH) at 25° C. Microscopic analysis of Form A1 showed it to contain particles of size 30-75 μm and showed bi-refringence.

According to another embodiment, the present invention provides a process for preparing Form A1, as exemplified herein below.

According to another embodiment, the present invention provides a process for preparing Form A1 by heating amorphous Compound 1 above its melting point to form a molten mass and then cooling said mass whereupon said mass recrystallizes to Form A1 between about 120° C. to about 160° C.

According to another embodiment, the present invention provides a method of converting polymorph Form B2 or Form C3 to Form A1 by exposing neat Form B2 or Form C3 to a suitable elevated temperature for a suitable period of time and then cooling to provide Form A1.

In another embodiment, increasing the temperature accelerates the transformation rate of Form B2 or Form C3 to Form A1. In another embodiment, the transformation rate is accelerated in the temperature range of about 20° C. to about 200° C. In yet another embodiment, the temperature ranges from about 30° C. to about 100° C.

According to another embodiment, the present invention provides a method of converting polymorph Form B2 or Form C3 to Form A1 by exposing a solution or slurry of Form B2 or Form C3 in a suitable solvent or mixtures of solvents to a suitable temperature for a suitable period of time and then cooling the slurry or solution and finally collecting the solid Form A1. In another embodiment said suitable solvent or mixture of solvents is selected from those solvents indicated in Table 1 herein below.

According to another embodiment, the present invention provides a method of converting mixtures of either Form A1 and B2, or Form A1 and C3, or Form B2 and C3 to Form A1 by heating at a suitable temperature for suitable period of time in a suitable solvent or mixture of solvents with suitable agitation. In one embodiment said suitable solvent(s) comprise ethyl acetate, 10% water/dioxane, 25% water/ethanol, or tetrahydrofuran, said suitable period of time is about 24 hours, and said suitable agitation comprises shaking.

According to another embodiment, the present invention provides a pharmaceutical composition comprising Form A1 and a pharmaceutically acceptable carrier or adjuvant.

According to another embodiment, the present invention provides a method of formulating a pharmaceutical composition comprising an amorphous form of Compound 1, comprising the steps of:
(i) converting Form A1 to an amorphous form; and
(ii) combining said amorphous form with one or more suitable pharmaceutical carrier or adjuvant.

According to another embodiment, the present invention provides a method of treating an IMPDH-mediated disease in a patient comprising the step of administering to said patient a therapeutically effective amount of Form A1 or a pharmaceutical composition comprising Form A1.

According to another embodiment, the present invention provides a process for preparing a polymorph of Form A1, said process comprising at least one of the following steps:
a) dissolving (S)-tetrahydrofuran-3-yl 3-(3-(3-methoxy-4-(oxazol-5-yl)phenyl)ureido)benzylcarbamate in a suitable solvent with suitable agitation at a suitable temperature to give a suitable solution;
b) adding a suitable volume of a suitable solvent over a suitable period of time, at a suitable temperature with agitation to generate a slurry;
c) cooling said slurry to a suitable temperature;
d) adding a suitable amount of the same solvent from step (b) to the slurry;
e) cooling said slurry to about room temperature;
f) filtering or centrifuging said slurry to give polymorph Form A;
g) rinsing said Form A a suitable number of times with a suitable solvent; and
h) drying said Form A at a suitable temperature under a suitable reduced pressure for a suitable period of time to constant weight.

According to another embodiment, the present invention provides a polymorphic Form B2 of (S)-tetrahydrofuran-3-yl 3-(3-(3-methoxy-4-(oxazol-5-yl)phenyl)ureido)benzylcarbamate.

According to another embodiment, the present invention provides a polymorphic Form B2 wherein the polymorph has a peak position at about 20.9 degrees 2-theta in an x-ray powder diffraction pattern obtained using Cu K alpha radiation.

According to another embodiment, the present invention provides a polymorphic Form B2 wherein the polymorph has at least one additional peak position at about 5.3, 15.7, 18.4, or 20.0 degrees 2-theta in an x-ray powder diffraction pattern obtained using Cu K alpha radiation.

According to another embodiment, the present invention provides a polymorphic Form B2 wherein the polymorph exhibits a broad endothermic event between about 80° C. and about 100° C. as measured by a Differential Scanning Calorimeter.

According to another embodiment, the present invention provides a polymorphic Form B2 wherein the polymorph exhibits a melting/recrystallization event at between about 146° C. and about 150° C. as measured by a Differential Scanning Calorimeter.

According to another embodiment, the present invention provides a polymorphic Form B2 wherein the polymorph exhibits a melting/decomposition endothermic event at about 215° C. as measured by a Differential Scanning Calorimeter.

According to another embodiment, polymorphic Form B2 is a crystalline form containing various solvent levels. DSC analysis shows three events; a broad, weak endotherm between 80° C. and 100° C. which is consistent with loss of solvent from the sample or a solid phase transition; a melting/re-crystallization event at about 146° C. to about 150° C.; and a final melting/decomposition endotherm with an onset of about 215° C. Microscopic analysis of Form B2 showed it to contain particles of size 30-75 μm and showed bi-refringence.

According to another embodiment, the present invention provides a process for preparing Form B2, as exemplified herein below.

According to another embodiment, the present invention provides a pharmaceutical composition comprising Form B2 and a pharmaceutically acceptable carrier or adjuvant.

According to another embodiment, the present invention provides a method of formulating a pharmaceutical composition comprising an amorphous form of Compound 1, comprising the steps of:
(i) converting Form B2 to an amorphous form; and
(ii) combining said amorphous form with one or more suitable, pharmaceutical carrier or adjuvant.

According to another embodiment, the present invention provides a method of treating an IMPDH-mediated disease in a patient comprising the step of administering to said patient a therapeutically effective amount of Form B2 or a pharmaceutical composition comprising Form B2.

According to another embodiment, the present invention provides a polymorphic Form B2 of (S)-tetrahydrofuran-3-yl 3-(3-(3-methoxy-4-(oxazol-5-yl)phenyl)ureido)benzylcarbamate.

According to another embodiment, the present invention provides a polymorphic Form B2 wherein the polymorph has a peak position at about 20.9 degrees 2-theta in an x-ray powder diffraction pattern obtained using Cu K alpha radiation.

According to another embodiment, the present invention provides a polymorphic Form B2 wherein the polymorph has at least one additional peak position at about 5.3, 15.7, 18.4, or 20.0 degrees 2-theta in an x-ray powder diffraction pattern obtained using Cu K alpha radiation.

According to another embodiment, the present invention provides a polymorphic Form B2 wherein the polymorph exhibits a broad endothermic event between about 80° C. and about 100° C. as measured by a Differential Scanning Calorimeter.

According to another embodiment, the present invention provides a polymorphic Form B2 wherein the polymorph exhibits a melting/recrystallization event at between about 146° C. and about 150° C. as measured by a Differential Scanning Calorimeter.

According to another embodiment, the present invention provides a polymorphic Form B2 wherein the polymorph exhibits a melting/decomposition endothermic event at about 215° C. as measured by a Differential Scanning Calorimeter.

According to another embodiment, the present invention provides a polymorphic Form C3 of (S)-tetrahydrofuran-3-yl 3-(3-(3-methoxy-4-(oxazol-5-yl)phenyl)ureido)benzylcarbamate.

According to another embodiment, the present invention provides a polymorphic Form C3 wherein the polymorph has a peak position at about 20.7 degrees 2-theta in an x-ray powder diffraction pattern obtained using Cu K alpha radiation.

According to another embodiment, the present invention provides a polymorphic Form C3 wherein the polymorph has at least one additional peak position at about 5.2, 15.5, 17.5, or 22.5 degrees 2-theta in an x-ray powder diffraction pattern obtained using Cu K alpha radiation.

According to another embodiment, the present invention provides a polymorphic Form C3 wherein the polymorph exhibits a melting/recrystallization event at between about 145° C. and about 160° C. as measured by a Differential Scanning Calorimeter.

According to another embodiment, Form C3 is an anhydrous crystalline form of Compound 1. Thermal analysis of the sample indicates that it undergoes a melt/re-crystallization transition at about 145° C.-160° C. Variable temperature XRPD confirms the transition from Form C3 to Form A1 between about 140° C. and about 160° C. Form C3 is moderately hygroscopic and exhibits 3% weight uptake at 90% relative humidity at 25° C.

According to another embodiment, the present invention provides a process for preparing Form C3, as exemplified herein below.

According to another embodiment, the present invention provides a pharmaceutical composition comprising Form C3 and a pharmaceutically acceptable carrier or adjuvant.

According to another embodiment, the present invention provides a method of formulating a pharmaceutical composition comprising an amorphous form of Compound 1, comprising the steps of:
(i) converting Form C3 to an amorphous form; and
(ii) combining said amorphous form with one or more suitable pharmaceutical carrier or adjuvant.

According to another embodiment, the present invention provides a method of treating an IMPDH-mediated disease in a patient comprising the step of administering to said patient a therapeutically effective amount of Form C3 or a pharmaceutical composition comprising Form C3.

According to another embodiment, the present invention provides a polymorphic Form D4 of (S)-tetrahydrofuran-3-yl 3-(3-(3-methoxy-4-(oxazol-5-yl)phenyl)ureido)benzylcarbamate, HCl salt.

According to another embodiment, the present invention provides a polymorphic Form D4 wherein the polymorph has a peak position at about 24.94 degrees 2-theta in an x-ray powder diffraction pattern obtained using Cu K alpha radiation.

According to another embodiment, the present invention provides a polymorphic Form D4 wherein the polymorph has at least one additional peak position at about 11.1, 15.7, 16.9, 18.8, or 27.4 degrees 2-theta in an x-ray powder diffraction pattern obtained using Cu K alpha radiation.

According to another embodiment, the present invention provides a polymorphic Form D4 wherein the polymorph exhibits a broad endothermic event between about 100° C. and about 170° C. as measured by a Differential Scanning Calorimeter.

According to another embodiment, Form D4 is a weakly crystalline HCl salt form of Compound 1. Microscopic analysis of Form D4 shows little birefringence typical of a weakly crystalline sample and upon heating of the sample a melt/decomposition is observed followed by a re-crystallization of the material. This change is confirmed by variable temperature XRPD analysis which shows a change in the pattern between 140° C. and 160° C. to an XRPD pattern that is similar to Form A1 of the free base. This is consistent with loss of the HCl from the salt and re-crystallization of the free base from the melt. Thermogravimetric analysis of the salt shows a weight loss of 6.5% up to 170° C. which is approximately (7.4% theoretical) the expected weight loss for loss of HCl from the salt. This loss of HCl from the sample manifests itself as a broad endotherm in the DSC from about 100° C. to about 170° C.

According to another embodiment, the present invention provides a process for preparing Form D4 as exemplified herein below.

According to another embodiment, the present invention provides a pharmaceutical composition comprising Form D4 HCl salt and a pharmaceutically acceptable carrier or adjuvant.

According to another embodiment, the present invention provides a method of formulating a pharmaceutical composition comprising an amorphous form of Compound 1, HCl salt, comprising the steps of:
(i) converting Form D4 to an amorphous form; and
(ii) combining said amorphous form with one or more suitable pharmaceutical carrier or adjuvant.

According to another embodiment, the present invention provides a method of treating an IMPDH-mediated disease in a patient comprising the step of administering to said patient a therapeutically effective amount of Form D4 HCl salt or a pharmaceutical composition comprising Form D4 HCl salt.

According to another embodiment, the present invention provides a polymorphic Form E5 of (S)-tetrahydrofuran-3-yl 3-(3-(3-methoxy-4-(oxazol-5-yl)phenyl)ureido)benzylcarbamate, HCl salt.

According to another embodiment, the present invention provides a polymorphic Form E5 wherein the polymorph has at least one peak position at about 14.8 degrees 2-theta in an x-ray powder diffraction pattern obtained using Cu K alpha radiation.

According to another embodiment, the present invention provides a polymorphic Form E5 wherein the polymorph has at least one additional peak position at about 19.4, 21.4, 22.5, or 25.4 degrees 2-theta in an x-ray powder diffraction pattern obtained using Cu K alpha radiation.

According to another embodiment, polymorphic Form E5 as an HCl salt, is a weakly crystalline salt form of Compound 1. Microscopic analysis of Form E5 shows little bi-refringence typical of a weakly crystalline sample and upon heating of the sample a melt/decomposition is observed followed by a re-crystallization of the material. The variable temperature XRPD analysis that shows a change in the pattern between about 120° C. and about 150° C. confirms this change. This is consistent with loss of the HCl from the salt and re-crystallization of the free base from the melt. Form E5 HCl salt is highly hygroscopic with an uptake of 22% w/w at 90% relative humidity. DSC analysis of the sample shows initial loss of water/solvent from the sample followed by melting and loss of HCl. The latter two events are confirmed by hot stage microscopy and thermogravimetric/variable temperature-XRPD.

According to another embodiment, the present invention provides a process for preparing Form E5 HCl salt, as exemplified herein below.

According to another embodiment, the present invention provides a pharmaceutical composition comprising Form E5 HCl salt and a pharmaceutically acceptable carrier or adjuvant.

According to another embodiment, the present invention provides a method of formulating a pharmaceutical composition comprising an amorphous form of Compound 1, comprising the steps of:
(i) converting Form E5 HCl salt to an amorphous form; and
(ii) combining said amorphous form with one or more suitable pharmaceutical carrier or adjuvant.

According to another embodiment, the present invention provides a method of treating an IMPDH-mediated disease in a patient comprising the step of administering to said patient a therapeutically effective amount of Form E5 HCl salt or a pharmaceutical composition comprising Form E5 HCl salt.

According to another embodiment, the present invention provides a substantially pure amorphous form of (S)-tetrahydrofuran-3-yl 3-(3-(3-methoxy-4-(oxazol-5-yl)phenyl)ureido)benzylcarbamate wherein said amorphous Form comprises less than 5% by weight of Form A1.

According to another embodiment, the present invention provides an amorphous form of (S)-tetrahydrofuran-3-yl 3-(3-(3-methoxy-4-(oxazol-5-yl)phenyl)ureido)benzylcarbamate.

According to another embodiment, the present invention provides a process to prepare an amorphous form of Compound 1 from Form B2 or Form C3 by evaporation of a solution of polymorphic Form B2 or Form C3 in a suitable solvent or a mixture of suitable solvents.

According to another embodiment, the present invention provides a process to prepare an amorphous Form HCl salt of Compound 1 from Form D4 HCl salt or Form E5 HCl salt by evaporation of a solution of Form D4 HCl salt or Form E5 HCl salt in a suitable solvent or a mixture of suitable solvents.

According to another embodiment, the present invention provides a process to prepare an amorphous form of Compound 1 from polymorphic Form A1 by evaporation of a solution of Form A1 in 2,2,2-trifluoroethanol or hexafluoroisopropanol or mixtures thereof.

According to another embodiment, the present invention provides a process to prepare an amorphous form of Compound 1 by cooling a molten sample of a crystalline form of (S)-tetrahydrofuran-3-yl 3-(3-(3-methoxy-4-(oxazol-5-yl) phenyl)ureido)benzylcarbamate. According to one embodiment, the amorphous form of Compound 1 is produced by converting a crystalline form of Compound 1, e.g., Form A1, into an amorphous form of Compound 1.

According to another embodiment, the present invention provides a pharmaceutical composition comprising the amorphous Form according to any of the embodiments herein, wherein said composition is produced by combining said amorphous form with one or more suitable pharmaceutical carriers or adjuvants.

According to another embodiment, the present invention provides a pharmaceutical composition comprising an amorphous form of Compound 1 and a pharmaceutical acceptable adjuvant or carrier.

According to one embodiment, the present invention provides a method of treating an IMPDH-mediated disease or condition in a mammal comprising the step of administering to said mammal a pharmaceutical composition containing Form A1, Form B2, Form C3, Form D4, Form E5 or amorphous form.

According to another embodiment, the present invention provides a method of treating an IMPDH-mediated disease or condition in a mammal comprising the step of administering to said mammal a pharmaceutical composition containing Form A1, Form B2, Form C3, Form D4, Form E5 or amorphous form.

According to another embodiment, the present invention provides a method for inhibiting viral replication in a mammal comprising the step of administering to said mammal a pharmaceutical composition containing Form A1, Form B2, Form C3, Form D4, Form E5 or amorphous form.

According to another embodiment, the present invention provides a method for treating a mammal suffering from a viral infection caused by a virus selected from hepatitis B virus, hepatitis C virus, orthomyxovirus, paramyxovirus, herpesvirus, retrovirus, flavivirus, pestivirus, hepatotrophic virus, bunyavirus, Hantaan virus, Caraparu virus, human papilloma virus, encephalitis virus, arena virus, reovirus, vesicular stomatitis virus, rhinovirus, entervirus, Lassa fever virus, togavirus, poxvirus, adenovirus, rubiola, or rubella.

Specific acid salts useful for producing salt forms of Compound 1, Form A1, Form B2, Form C3, and amorphous form and for producing salts other than the HCl salt for Form D4 and E5 may be selected from acids known in the art. See, e.g., "Practical Process, Research & Development," Anderson, Neal G., Academic Press, 2000, the contents of which is incorporated herein by reference.

The term "suitable" as used herein, describes solvent, temperature, filtrate, agitation, solution, medium, quantity, period of time, etc. Such suitable solvents, temperature, filtrate, agitation, solution, medium, quantity, period of time, etc. are readily known to one of skill in the art.

The term "pharmaceutically acceptable carrier or adjuvant" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and $N^+(C_{1-4}\ alkyl)_4$ salts. This invention also envisions the quaternization of any basic nitrogen-containing groups of the compounds disclosed herein. Water or oil-soluble or dispersible products may be obtained by such quaternization.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

In one embodiment, the pharmaceutically acceptable compositions of this invention are formulated for oral administration.

The amount of the compounds of the present invention that may be combined with the carrier materials to produce a composition in a single dosage form will vary depending upon the host treated, the particular mode of administration. Preferably, the compositions should be formulated so that a dosage of between 0.01-100 mg/kg body weight/day of the compound can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Depending upon the particular condition, or disease, to be treated or prevented, additional therapeutic agents, which are normally administered to treat or prevent that condition, may also be present in the compositions of this invention. As used herein, additional therapeutic agents that are normally administered to treat or prevent a particular disease, or condition, are known as "appropriate for the disease, or condition, being treated."

When the compositions of this invention comprise a combination of an IMPDH inhibitor of this invention and one or more additional therapeutic or prophylactic agents, such as those disclosed herein, both the IMPDH inhibitor and the additional agent(s) should be present at dosage levels of between about 10 to 100%, and more preferably between about 10 to 80% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

When the compositions of this invention comprise a combination of an IMPDH inhibitor of this invention and one or more additional therapeutic or prophylactic agents, both the compound and the additional agent should be present at dosage levels of between about 10 to 100% and in another embodiment between about 10 to 80% of the dosage normally administered in a monotherapy regimen.

According to one embodiment, the pharmaceutical compositions of this invention comprise an additional immunosuppression agent. Examples of additional immunosuppression agents include, but are not limited to, cyclosporin A, FK506, rapamycin, leflunomide, deoxyspergualin, prednisone, azathioprine, mycophenolate mofetil, OKT3, ATAG, mizoribine, and interferon including alpha-interferon such as PEG-Intron® and Pegasys®.

The term "interferon" as used herein means a member of a family of highly homologous species-specific proteins that inhibit viral replication and cellular proliferation, and modulate immune response, such as interferon alpha, interferon beta, or interferon gamma. The Merck Index, entry 5015, Twelfth Edition.

According to one embodiment of the present invention, the interferon is a-interferon. According to another embodiment, a therapeutic combination of the present invention utilizes natural alpha interferon 2a. Or, the therapeutic combination of the present invention utilizes natural alpha interferon 2b. In another embodiment, the therapeutic combination of the present invention utilizes recombinant alpha interferon 2a or 2b. In yet another embodiment, the interferon is pegylated alpha interferon 2a or 2b. Interferons suitable for the present invention include:

(a) Intron (interferon-alpha 2B, Schering Plough),
(b) Peg-Intron,
(c) Pegasys,
(d) Roferon,
(e) Berofor,
(f) Sumiferon,
(g) Wellferon,
(h) consensus alpha interferon available from Amgen, Inc., Newbury Park, Calif.,
(i) Alferon;
(j) Viraferon®; and
(k) Infergen®.

According to an alternate embodiment, the pharmaceutical compositions of this invention may additionally comprise an anti-cancer agent. Examples of anti-cancer agents include, but are not limited to, cis-platin, actinomycin D, doxorubicin, vincristine, vinblastine, etoposide, amsacrine, mitoxantrone, tenipaside, taxol, colchicine, cyclosporin A, phenothiazines, interferon and thioxantheres.

In another embodiment, the compositions of this invention additionally comprise another anti-viral agent, including an anti-HCV agent. Such anti-viral agents include, but are not limited to, immunomodulatory agents, such as α-, β-, and γ-interferons, pegylated derivatized interferon-α compounds, and thymosin; other anti-viral agents, such as ribavirin (and the combination therapy of ribavirin and pegylated interferon [Rebetrol®]), d4T, ddI, AZT, amprenavir, fos-amprenavir, acyclovir, NS3-NS4A protease inhibitors such as those disclosed in PCT publication No. WO 02/018369, amantadine, cytovene, ganciclovir, ritonivir, trisodium phosphonoformate, and telbivudine; other inhibitors of hepatitis C proteases (NS2-NS3 inhibitors and NS3-NS4A inhibitors); inhibitors of other targets in the HCV life cycle, including but not limited to, helicase and polymerase inhibitors; inhibitors of internal ribosome entry; and broad-spectrum viral inhibitors, such as IMPDH inhibitors (e.g., IMPDH inhibitors disclosed in U.S. Pat. Nos. 5,807,876 and 6,498,178, mycophenolic acid and derivatives thereof).

In another embodiment, the compositions of this invention additionally comprise another anti-viral agent selected from alpha-interferon, pegylated alpha-interferon, or ribavirin.

In one embodiment, the compositions of this invention additionally comprise another agent, including a cytochrome P-450 inhibitor. Such cytochrome P-450 inhibitors include, but are not limited to, ritonavir. CYP inhibitors may be useful in increasing liver concentrations and/or increasing blood levels of compounds that are inhibited by CYP.

If an embodiment of this invention involves a CYP inhibitor, any CYP inhibitor that improves the pharmacokinetics of the IMPDH inhibitor may be used in a method of this invention. These CYP inhibitors include, but are not limited to, ritonavir (WO 94/14436), ketoconazole, troleandomycin, 4-methyl pyrazole, cyclosporin, clomethiazole, cimetidine, itraconazole, fluconazole, miconazole, fluvoxamine, fluoxetine, nefazodone, sertraline, indinavir, nelfinavir, amprenavir, fosamprenavir, saquinavir, lopinavir, delavirdine, erythromycin, VX-944, and VX-497. Preferred CYP inhibitors include ritonavir, ketoconazole, troleandomycin, 4-methyl pyrazole, cyclosporin, and clomethiazole. For preferred dosage forms of ritonavir, see U.S. Pat. No. 6,037,157, and the documents cited therein: U.S. Pat. No 5,484,801, U.S. application Ser. No. 08/402,690, and International Applications WO 95/07696 and WO 95/09614).

Methods for measuring the ability of a compound to inhibit cytochrome P450 monooxygenase activity are known (see U.S. Pat No. 6,037,157 and Yun, et al. *Drug Metabolism & Disposition*, vol. 21, pp. 403-407 (1993).

According to yet another alternate embodiment, the pharmaceutical compositions of this invention may additionally comprise an anti-vascular hyperproliferative agent. Examples of anti-vascular hyperproliferative agents include, but are not limited to, HMG Co-A reductase inhibitors such as lovastatin, thromboxane A2 synthetase inhibitors, eicosapentanoic acid, ciprostene, trapidil, ACE inhibitors, low molecular weight heparin, mycophenolic acid, rapamycin and 5-(3'-pyridinylmethyl)benzofuran-2-carboxylate.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. Patients may, however, require intermittent treatment on a long-term basis upon any recurrence of disease symptoms.

According to one embodiment, the term "IMPDH-mediated disease" as used herein includes immune system related diseases such as transplant rejection (e.g., kidney, liver, heart, lung, pancreas (islet cells), bone marrow, cornea, small bowel and skin allografts and heart valve xenografts), graft versus host disease, and autoimmune diseases, such as rheumatoid arthritis, multiple sclerosis, juvenile diabetes, asthma, inflammatory bowel disease (Crohn's disease, ulcerative colitis), lupus, diabetes, mellitus myasthenia gravis, psoriasis, dermatitis, eczema, seborrhea, pulmonary inflammation, eye uveitis, Grave's disease, Hashimoto's thyroiditis, Behcet's or Sjorgen's syndrome (dry eyes/mouth), pernicious or immunohaemolytic anaemia, idiopathic adrenal insufficiency, polyglandular autoimmune syndrome, glomerulonephritis, scleroderma, lichen planus, viteligo (depigmentation of the skin), autoimmune thyroiditis, and alveolitis.

According to another embodiment, the term "IMPDH-mediated disease" as used herein includes viral diseases such as DNA and RNA viral diseases caused by infection for example, by orthomyxoviruses (influenza viruses types A and B), paramyxoviruses (respiratory syncytial virus (RSV), subacute sclerosing panencephalitis (SSPE) virus) measles and parainfluenza type 3), herpesviruses (HSV-1, HSV-2, HHV-6, HHV-7, HHV-8, Epstein Barr Virus (EBV), cytomegalovirus (HCMV) and varicella zoster virus (VZV)), retroviruses (HIV-1, HIV-2, HTLV-1, HTLV-2), flavi- and pestiviruses (yellow fever virus (YFV), hepatitis C virus (HCV), dengue fever virus, bovine viral diarrhea virus (BVDV), hepatotrophic viruses (hepatitis A virus (HAV), hepatitis B virus (HBV), hepatitis D virus (HDV), hepatitis E virus (HEV), hepatitis G virus (HGV), Crimean-Congo hemorrhagic fever virus (CCHF), bunyaviruses (Punta Toro virus, Rift Valley fever virus (RVFV), and sandfly fever Sicilian virus), Hantaan virus, Caraparu virus), human papilloma viruses, encephalitis viruses (La Crosse virus), arena viruses (Junin and Tacaribe virus), reovirus, vesicular stomatitis virus, rhinoviruses, enteroviruses (polio virus, coxsackie viruses, encephalomyocarditis virus (EMC)), Lassa fever virus, and togaviruses (Sindbis and Semlike forest viruses) and poxviruses (vaccinia virus), adenoviruses, rubiola, and rubella.

According to another embodiment, the term "IMPDH-mediated disease" as used herein includes vascular cellular hyperproliferative diseases such as restenosis, stenosis, artherosclerosis and other hyperproliferative vascular disease.

According to another embodiment, the term "IMPDH-mediated disease" as used herein includes tumors and malignancies, such as lymphoma, leukemia and other forms of cancer such as breast cancer, prostate cancer, colon cancer, pancreatic cancer, etc.

According to another embodiment, the term "IMPDH-mediated disease" as used herein includes inflammatory diseases such as osteoarthritis, acute pancreatitis, chronic pancreatitis, asthma and adult respiratory distress syndrome.

Suitable methods for the conversion of a crystalline form, such as a polymorphic form of the present invention, into an amorphous form suitable for formulation are well known in the art. See, e.g., "Remington: The Science & Practice of Pharmacy"; Alfonso R. Gennaro, Editor, Mack Publishing, 1995, 19th Edition, Volume 2, the entire disclosure whereof is incorporated herein by reference.

In order that the invention described herein may be more fully understood, the following experimental methods, assays, and examples are set forth. The following experimental methods, assays, and examples are offered by way of illustration, not limitation.

Experimental Methods

X-RAY Powder Diffraction (XRPD)

X-ray powder diffraction patterns for the samples were acquired on a Bruker AXS/Siemens D5000 diffractometer using CuKα radiation (40 kV, 40 mA), ?-? goniometer, automatic divergence and receiving slits, a graphite secondary monochromator and a scintillation counter. The data were collected over an angular range of 2° to 42° 2? in continuous scan mode using a step size of 0.02° 2? and a step time of 1 second. Samples run under ambient conditions were prepared as flat plate specimens using powder as received without grinding. Approximately 25-50 mg of the sample was gently packed into 12 mm diameter, 0.5 mm deep cavities cut into polished, zero-background (510) silicon wafers (The Gem Dugout, 1652 Princeton Drive, Pennsylvania State College, PA 16803, USA). All specimens were run both stationary and rotated in their own plane during analysis. A further specimen was run using silicon powder as an internal standard to correct for any peak displacement. Samples run under non-ambient conditions were packed into a stainless steel cavity sample holder equipped with a Pt 100 thermocouple for temperature monitoring. Low temperature data were recorded using an Anton Paar TTK450 variable temperature camera attached to the Bruker AXS/Siemens D5000 diffractometer. Instrumental conditions for the low temperature scan were similar to those described for the flat plate samples above. All XRPD analyses were performed using the Diffrac Plus XRD Commander software v2.3.1. Diffraction data are reported using Cu K$\alpha_1$ ($\lambda$=1.5406 Å), after the K$\alpha_2$ component had been stripped using EVA, the powder patterns were indexed by the ITO method using WIN-INDEX and the raw lattice constants refined using WIN-METRIC.

Alternatively, X-ray powder diffraction patterns for the samples were acquired on a Bruker AXS C2 GADDS diffractometer using Cu K$\alpha$ radiation (40 kV, 40 mA), automated XYZ stage, laser video microscope for auto-sample positioning and a HiStar 2-dimensional area detector. X-ray optics consists of a single Göbel multilayer mirror coupled with a pinhole collimator of 0.3 mm. Beam divergence, i.e. the effective size of the X-ray beam on the sample, was approximately 4 mm. A ?-? continuous scan mode was employed with a sample to detector distance of 20 cm which gives an effective 2? range of 3.2-29.8°. A typical exposure time of a sample would be 120 s. Samples run under ambient conditions were prepared as flat plate specimens using powder as received without grinding. Approximately 1-2 mg of the sample was lightly pressed on a glass slide to obtain a flat surface. Samples run under non-ambient conditions were mounted on a silicon wafer with heat conducting compound. The sample was then heated to the appropriate temperature at approximately 20° C./minute and subsequently held isothermally for approximately 1 minute before data collection was initiated Differential Scanning Calorimetry (DSC)

Differential scanning calorimetry data was collected on a TA instrument Q1000 equipped with a 50 position autosampler. The energy and temperature calibration standard was indium. Samples were heated at a rate of 10° C./min between 10 and 230° C. A nitrogen purge at 30 ml/min was maintained over the sample. Between 1 and 3 mg of sample was used, unless otherwise stated, and all samples crimped in a hermetically sealed aluminium pan.

Hot Stage Microscopy

Hot stage microscopy was studied using a Leica LM/DM polarised microscope combined with a Mettler-Toledo MTFP82HT hot-stage in the temperature range 25-230° C. with typical heating rates in the range 10-20° C./min. A small amount of sample was dispersed onto a glass slide with individual particles separated as well as possible. Samples were viewed under normal or cross-polarised light (coupled to a $\lambda$ false-colour filter) with a ×20 objective lens.

Thermogravimetric Analysis (TGA)

TGA data was collected a TA Instrument Q500 TGA, calibrated with Nickel/Alumel and running at scan rates of 10° C./minute. A nitrogen purge at 60 ml/min was maintained over the sample. Typically 10-20 mg of sample was loaded onto a pre-tared platinum crucible.

Infra-Red Spectroscopy by FT-IR (IR)

Samples were studied on a Perkin-Elmer Spectrum One fitted with a Universal ATR sampling accessory. The data was collected and analysed using Spectrum V5.0.1 software.

Fast Evaporation (FE)

Solutions were prepared in various solvents and sonicated between aliquot additions to assist in dissolution. Once a mixture reached complete dissolution, as judged by visual observation, the solution was filtered through a 0.2 µm nylon filter. The filtered solution was allowed to evaporate at ambient temperature in an open vial. The solids that formed were isolated and analyzed.

Slow Evaporation (SE)

Solutions were prepared in various solvents and sonicated between aliquot additions to assist in dissolution. Once a mixture reached complete dissolution, as judged by visual observation, the solution was filtered through a 0.2 µm nylon filter. The filtered solution was allowed to evaporate at ambient temperature in a vial covered with aluminum foil perforated with pinholes. The solids that formed were isolated and analyzed.

Slow Cool (SC)

Saturated solutions were prepared in various solvents at elevated temperatures (approximately 60° C.) and filtered through a 0.2 µm nylon filter into an open vial while still warm. The vial was covered and allowed to cool slowly to room temperature. The presence or absence of solids was noted. If there were no solids present, or if the amount of solids was judged too small for XRPD analysis, the vial was placed in a refrigerator overnight. Again, the presence or absence of solids was noted and if there were none, the vial was placed in a freezer overnight. Solids that formed were isolated by filtration and allowed to dry prior to analysis.

Rotary Evaporation

Solutions were prepared in various solvents. The solution was then filtered into a round bottom flask and the solvent was removed by rotary evaporation. Solids were recovered and analyzed.

Cold Precipitation

Solutions were prepared in various solvents at elevated temperature (approximately 60° C.) and filtered through a 0.2-µm nylon filter into an antisolvent at sub-ambient temperature (an ice-water bath at approximately 0° C. when water was used, and a dry ice/acetone bath at approximately −78° C. for all other solvents). The resulting solids were isolated by filtration and dried prior to analysis.

Slurry Experiments (SE)

Solutions were prepared by adding enough solids to a given solvent so that undissolved solids were present. The mixture was then agitated in a sealed vial at a given temperature. After a given amount of time, the solids were isolated by suction filtration and analyzed.

In order that this invention be more fully understood, the following examples are offered by way of illustration, not limitation.

Assays

IMPDH Activity Inhibition Assay

IMP dehydrogenase activity was assayed following an adaptation of the method first reported by Magasanik. [B. Magasanik et al., *J. Biol. Chem.*, 226, p. 339 (1957), the disclosure of which is herein incorporated by reference]. Enzyme activity was measured spectrophotometrically, by monitoring the increase in absorbance at 340 nm due to the formation of NADH ($\lambda$340 is 6220 $M^{-1}$ $cm^{-1}$). The reaction mixture contained 0.1 M potassium phosphate 8.0, 0.5 mM EDTA, 2 mM DTT, 200 µM IMP and enzyme (IMPDH human type II) at a concentration of 15 to 50 nM. This solution is incubated at 37° C. for 10 minutes. The reaction is started by adding NAD to a final concentration of 200 µM and the initial rate is measured by following the linear increase in absorbance at 340 nm for 10 minutes. For reading in a standard spectrophotometer (path length 1 cm) the final volume in the cuvette is 1.0 ml. The assay has also been adapted to a 96 well microtiter plate format; in this case the concentrations of all the reagents remain the same and the final volume is decreased to 200 µl. For the analysis of inhibitors, the compound in question is dissolved in DMSO to a final concentration of 20 mM and added to the initial assay mixture for preincubation with the enzyme at a final volume of 2-5% (v/v). The reaction is started by the addition of NAD, and the initial rates measured as above. $K_i$ determinations are made by measuring the initial velocities in the presence of varying amounts of inhibitor and fitting the data using the tight-binding equations of Henderson (Henderson, P. J. F. (1972) Biochem. J. 127, 321).

Cellular Assays

A. Isolation of peripheral blood mononuclear cells (PBMCs): Human venous blood was drawn from normal healthy volunteers using heparin as an anti-coagulant. PBMCs were isolated from blood by centrifugation over Ficoll-paque gradient or CPT tubes (Becton-Dickinson) using standard conditions. PBMCs were harvested, washed and re-suspended in complete RPMI, counted and diluted to $1 \times 10^6$ cells/mL.

B. PBMC and splenocyte proliferation assays: $5 \times 10^4$ cells (for human PBMC T cells) or $1 \times 10^5$ cells (for human PBMC B cells) were added per well of a 96-well plate. For T-cell assays, phyto-hemagglutinin (PHA) was added to a final concentration of 10-20 µg/mL per well for cell. For B-cell assays, *Staphylococcal* protein A (SPAS) was added to a final concentration of 2 µg/mL per well. Serial 4-fold dilutions of inhibitor stocks were made in complete RPMI media and added to cells such that the final concentration of compounds ranged from 20 µM to 20 nM, while DMSO was maintained at a final concentration of 0.1%. The cells were then incubated for 3 days. All samples were tested in triplicate. Tritiated thymidine (0.4 µCi/well) was added for the last 24 hours of the assay. The cells were harvested onto Betaplate filters and counted in a scintillation counter. Concentrations of compounds required to inhibit proliferation of cells by 50% (IC50 values) were calculated using the SoftMax Pro™ (Molecular Devices) computer software package.

Anti-Viral Assays

The anti-viral efficacy of compounds may be evaluated in various in vitro and in vivo assays. For example, compounds may be tested in in vitro viral replication assays. In vitro assays may employ whole cells or isolated cellular components. In vivo assays include animal models for viral diseases. Examples of such animal models include, but are not limited to, rodent models for HBV or HCV infection, the Woodchuck model for HBV infection, and chimpanzee model for HCV infection.

Abbreviations and terms which are used in the examples that follow and throughout the specification include:

| | |
|---|---|
| EtOAc: | ethyl acetate |
| i-BuOAc: | isobutyl acetate |
| i-PrOAc: | isopropyl acetate |
| MEK: | methyl ethyl ketone |
| MIBK: | methyl isobutyl ketone |
| TBME: | tert-butyl methyl ether |
| MeOH: | methanol |
| EtOH: | ethyl alcohol |
| TFE: | 2,2,2-trifluoroethanol |
| IPA: | isopropyl alcohol |
| HFIPA: | hexafluoroisopropanol |
| ACN: | acetonitrile |
| THF: | tetrahydrofuran |
| NMP: | N-methylpyrrolidinone |
| DMF: | N,N-dimethylformamide |
| DMSO: | dimethylsulfoxide |
| HCl: | hydrochloric acid |
| $N_2$: | nitrogen gas |
| L: | liter |
| ml: | milliliter |
| $T_{max}$: | maximum temperature |

-continued

| | |
|---|---|
| g: | gram |
| Kg: | kilogram |
| mg: | milligram |
| M: | molar |
| VT: | variable temperature |
| PBMC: | peripheral blood mononuclear cells |
| PHA: | phyto-hemagglutinin |
| SPAS: | Staphylococcal protein A |
| DTT: | dithiothreitol |
| EDTA: | ethylenediaminetetraacetic acid |
| NAD: | nicotinamide adenine dinucleotide |
| CPT: | cell preparation tube |
| RPMI: | Roswell Park Memorial Institute |
| HBV: | hepatitis B virus |
| HCV: | hepatitis C virus |

EXAMPLES

Example 1

Compound 1 used to prepare the polymorphs of this invention may be synthesized using the methods described in the Compound 1 patents. In addition, Compound 1 of this invention may be prepared by standard manipulations of methods known to those skilled in the art Example 2

Preparation of Form A1

1.8 g of Compound 1 in 3.6 ml of N-methylpyrrolidinone in a 50 ml round bottom flask was heated to 60° C. Four volumes (7.2 ml) of methanol was added and crystallization soon became evident at 60° C. The suspension was cooled to 50° C., additional methanol (14.4 ml) was added and the mixture finally cooled to room temperature and filtered. The filtrate was washed with methanol twice (3.6 ml each), then dried in vacuo to give 1.65 g of Form A1 (92% yield).

Example 3

Maturation Study of Form A1

Approximately 10 mg of Form A1 was slurried in 500 µl of solvent (see Table 1 below) and shaken at 25-30° C. for 24 hrs. The excess solid was removed by filtration and analysed by XRPD. The results of the XRPD analysis after 24 hrs are shown in Table 1 below. From all the 31 solvents screened in Table 1, the XRPD patterns observed were consistent with the pattern of Form A1.

TABLE 1

| Expt No | Solvent | XRPD Pattern |
|---|---|---|
| 1 | Acetone | A1 |
| 2 | 1-butanol | A1 |
| 3 | 2-butanol | A1 |
| 4 | butyl acetate | A1 |
| 5 | TBME | A1 |
| 6 | EtOH | A1 |
| 7 | EtOAc | A1 |
| 8 | Ethyl formate | A1 |
| 9 | heptane | A1 |
| 10 | i-BuOAc | A1 |
| 11 | i-PrOAc | A1 |
| 12 | 3-methyl-1-butanol | A1 |
| 13 | MEK | A1 |

TABLE 1-continued

| Expt No | Solvent | XRPD Pattern |
|---|---|---|
| 14 | MIBK | A1 |
| 15 | 2-methyl-1-propanol | A1 |
| 16 | 1-pentanol | A1 |
| 17 | 1-propanol | A1 |
| 18 | IPA | A1 |
| 19 | propyl acetate | A1 |
| 20 | THF | A1 |
| 21 | ACN | A1 |
| 22 | Toluene | A1 |
| 23 | MeOH | A1 |
| 24 | 10% H2O/MeOH | A1 |
| 25 | 10% H2O/EtOH | A1 |
| 26 | 10% H2O/IPA | A1 |
| 27 | 10% H2O/ACN | A1 |
| 28 | 10% H2O/THF | A1 |
| 29 | 10% H2O/acetone | A1 |
| 30 | 10% H2O/dioxane | A1 |
| 31 | 10% H2O/butanol | A1 |

Example 4

Crystallization Experiments with Compound 1

Table 2 below provides a summary of crystallization experiments carried out on Compound 1 using various solvents and conditions described herein. The resulting Form A1 or amorphous form obtained were dried in vacuo then analyzed by XRPD.

TABLE 2

| Solvent | Conditions[a] | Habit/Description | XRPD Result[b] |
|---|---|---|---|
| acetone | slurry | white solid | A1 |
| ACN | slurry | white solid | A1 |
| CH$_2$Cl$_2$ | SC | white birefringent fibers | amorphous |
|  | slurry | off white solid | A1 |
| diethyl ether | slurry | white solid | A1 |
| DMF | FE | white residue, no extinguishment | A1 |
|  | SE | white chunks, no extinguishment | A1 |
| 1,4-dioxane | SC | No solids | — |
|  | slurry | white solid | A1 |
| EtOH | SC | white fibers | A1 |
|  | slurry | white solid | A1 |
| EtOAc | slurry | white solid | A1 |
| HFIPA | FE | white residue, no extinguishment | amorphous |
|  | SE | white residue, no extinguishment | amorphous |
|  | rotovap | off white solid | amorphous |
| hexanes | slurry | white solid | A1 |
| IPA | SC | white irregular bits, no birefringence | A1 |
|  | slurry | white solid | A1 |
| MeOH | SC | rosettes of white fibers | A1 |
|  | slurry | white solid | A1 |
| THF | FE | white dendridics, some extinguishment | A1 (LC) |
|  | SE | — | — |
|  |  | off white solid | A1 |
| toluene | slurry | white solid | A1 |
| 2,2,2-TFE | FE | — | — |
|  |  | irregulars, no extinguishment | A1 |
|  | SE | white round granules, no extinguishment | A1 |
|  | SC | white chunks, no birefringence | A1 (LC) |
| trifluorotoluene | slurry | white solid | A1 |

[a]FE = fast evaporation; SE = slow evaporation; SC = slow cool, rotovap = rotary evaporation
[b]LC = low crystallinity;

Example 5

Preparation of Form B2 by Cold Precipitation

Form B2 was obtained from a cold precipitation experiment involving DMF as the solvent and toluene or ethyl acetate as the anti-solvent. Therein a solution of Compound 1 in DMF at approximately 60° C. was filtered through a 0.2-μm nylon filter into toluene at approximately −78° C. The resulting solids were isolated by filtration and dried to give Form B2. XRPD analysis was consistent with Form B2.

Example 6

Preparation of Form B2 by Cold Precipitation 500 mg of Form A1 was dissolved in DMF (3.5 ml) at ambient temperature to obtain a clear solution. The clear solution was filtered to remove any undissolved Form A1. The clear solution was added to ethyl acetate (150 ml) at −78° C. The resulting mixture was placed at −20° C. for 5 days.

Precipitated solid was collected by filtration under vacuum and dried at 40° C. in vacuo to give Form B2 as a white solid. XRPD analysis was consistent with Form B2.

Example 7

Preparation of Form C3 by Heating

A sample of Form C3 was generated by heating a sample of polymorph Form B2 at 100° C. for one hour. XRPD analysis was consistent with Form C3.

Example 8

Preparation of Form D4, HCl salt 30 mg of Compound 1 was dissolved in 2 ml of a 50:50 mix of 5M HCl in isopropyl alcohol and 1M HCl in acetic acid at room temperature. A small portion of residual solid was removed by filtration. t-Butyl methyl ether (3 ml) was added to the clear solution and the sample placed at −20° C. overnight. The white solid present was collected by filtration and then vacuum-dried at room temperature to give Form D4 as an HCl salt. XRPD analysis was consistent with Form D4, HCl salt.

Example 9

Preparation of Form D4, HCl salt 30 mg of Compound 1 was dissolved in 2 ml of a 50:50 mix of 5M HCl in isopropyl alcohol and 1M HCl in acetic acid at room temperature. A small portion of residual solid was removed by filtration. t-Butyl methyl ether (3 ml) was added to the clear solution and the sample placed at −20° C. overnight. The white solid present was collected by filtration and then vacuum-dried at room temperature to give Form D4 as an HCl salt. XRPD analysis was consistent with Form D4, HCl salt.

Example 10

Preparation of Form E5, HCl Salt 200 mg of Compound 1 was dissolved in 10 ml of 37.5% wt HCl solution. Water (10 ml) was added and a white precipitate was immediately evident. The slurry was placed at 0-5° C. and stirred for 1 hour. Precipitated solid was collected by filtration, air dried under vacuum for 2 hrs and dried in vacuo at 40° C. for 3 days to give Form E5 as an HCl salt. XRPD analysis was consistent with Form E5, HCl salt.

Example 11

Preparation of Amorphous Material from Form A1

130 mg of Compound 1 (Form A1) was dissolved in 2,2,2-trifluoroethanol (6 ml) at room temperature to give a clear solution. Toluene was added (1 volume) and the solution was concentrated to dryness on a rotary evaporator to give an amorphous solid. The sample was dried in vacuo for 24 hrs at 40° C. After oven drying the sample was ground with a mortar and pestle to increase the amorphicity. XRPD analysis was consistent with amorphous form.

We claim:

1. A polymorphic Form A1 of (S)-tetrahydrofuran-3-yl 3-(3-(3-methoxy-4-(oxazol-5-yl)phenyl)ureido)benzylcarbamate wherein said polymorph is characterized by peak positions at about 21.8, 11.8, 16.0, 18.5, 20.1 and 23.6 degrees 2-theta in an x-ray powder diffraction pattern obtained using Cu K alpha radiation.

2. The polymorphic Form A1 according to claim 1, wherein the polymorph exhibits a melting/decomposition endothermic event at about 215° C. as measured by a Differential Scanning Calorimeter.

3. A polymorphic Form A1 of (S)-tetrahydrofuran-3-yl 3-(3-(3-methoxy-4-(oxazol-5-yl)phenyl)ureido)benzylcarbamate wherein said polymorph exhibits a melting/decomposition endothermic event at about 215° C. as measured by a Differential Scanning Calorimeter.

4. A polymorphic Form A1, wherein said polymorphic Form A1 has a peak position at about 21.8 degrees 2-theta in an x-ray powder diffraction pattern obtained using Cu K alpha radiation.

5. A polymorphic Form A1, wherein said polymorphic Form A1 has peak position at about 11.8 degrees 2-theta in an x-ray powder diffraction pattern obtained using Cu K alpha radiation.

6. A polymorphic Form A1, wherein said polymorphic Form A1 has peak position at about 16.0 degrees 2-theta in an x-ray powder diffraction pattern obtained using Cu K alpha radiation.

7. A polymorphic Form A1, wherein said polymorphic Form A1 has peak position at about 18.5 degrees 2-theta in an x-ray powder diffraction pattern obtained using Cu K alpha radiation.

8. A polymorphic Form A1, wherein said polymorphic Form A1 has peak position at about 20.1 degrees 2-theta in an x-ray powder diffraction pattern obtained using Cu K alpha radiation.

9. A polymorphic Form A1, wherein said polymorphic Form A1 has peak position at about 23.6 degrees 2-theta in an x-ray powder diffraction pattern obtained using Cu K alpha radiation.

10. A polymorphic Form A1, wherein said polymorphic Form A1 is characterized by an x-ray powder diffraction pattern as shown in FIG. 1.

* * * * *

UNITED STATES PATENT AND TRADEMARK OFFICE
CERTIFICATE OF CORRECTION

PATENT NO. : 7,605,270 B2  Page 1 of 1
APPLICATION NO. : 11/429811
DATED : October 20, 2009
INVENTOR(S) : Todd Blythe et al.

It is certified that error appears in the above-identified patent and that said Letters Patent is hereby corrected as shown below:

Title Page, Item (54) and at Column 1, lines 1-4, the title reads:

POLYMORPHIC FORMS OF (S).-1-TETRAHYDROFURAN-3-YL-3-(3-(3-METHOXY-4-(OXAZOL-5-YL)PHENYL)UREIDO)BENZYL CARBAMATE please replace with:

POLYMORPHIC FORMS OF (S)-1-TETRAHYDROFURAN-3-YL-3-(3-(3-METHOXY-4-(OXAZOL-5-YL)PHENYL)UREIDO)BENZYL CARBAMATE

Signed and Sealed this

First Day of December, 2009

David J. Kappos
*Director of the United States Patent and Trademark Office*